US009086362B2

(12) United States Patent
McMillan

(10) Patent No.: US 9,086,362 B2
(45) Date of Patent: Jul. 21, 2015

(54) LAYERED COMPOSITE COMPONENTS

(75) Inventor: Alison J. McMillan, Uttoxeter (GB)

(73) Assignee: ROLLS-ROYCE plc, London (GB)

( * ) Notice: Subject to any disclaimer, the term of this patent is extended or adjusted under 35 U.S.C. 154(b) by 546 days.

(21) Appl. No.: 13/419,020

(22) Filed: Mar. 13, 2012

(65) Prior Publication Data

US 2012/0247209 A1 Oct. 4, 2012

(30) Foreign Application Priority Data

Mar. 30, 2011 (GB) .................................. 1105348.5

(51) Int. Cl.
*G01N 29/04* (2006.01)
*G01N 29/12* (2006.01)
*G01N 29/34* (2006.01)

(52) U.S. Cl.
CPC ............... *G01N 29/12* (2013.01); *G01N 29/348* (2013.01); *G01N 2291/0231* (2013.01)

(58) Field of Classification Search
CPC ....................... G01N 29/12; G01N 2291/0231
USPC ........................................... 73/588, 596, 602
See application file for complete search history.

(56) References Cited

U.S. PATENT DOCUMENTS

| 4,457,174 A | 7/1984 | Bar-Cohen et al. |
| 6,260,415 B1 * | 7/2001 | Goebel et al. .................... 73/588 |
| 7,449,003 B2 * | 11/2008 | Fehre et al. ....................... 601/2 |
| 2007/0044561 A1 | 3/2007 | Engstrand et al. |

FOREIGN PATENT DOCUMENTS

| EP | 0 515 734 A1 | 12/1992 |
| EP | 1 750 123 A2 | 2/2007 |

OTHER PUBLICATIONS

Jul. 1, 2011 Search Report issued in British Application No. 1105348.5.

* cited by examiner

*Primary Examiner* — John Chapman, Jr.
(74) *Attorney, Agent, or Firm* — Oliff PLC

(57) ABSTRACT

A method is provided that enables the identification of a region of a layered composite component that a test signal has passed through. The method comprises applying a label to the test signal as it passes through the region, such that the label applied to the test signal is indicative of the said region. The labelled signal can be identified by a sensor, even if the signal is of low strength and amongst a lot of noise, such as that caused by the multiple reflections and refractions that take place when an acoustic signal passes through a layered composite component.

10 Claims, 3 Drawing Sheets

LAYERED COMPOSITE COMPONENTS

The present invention relates to layered composite components and in particular to the propagation of signals, such as acoustic signals, through such components. Layered composite components are employed in many applications, for example in gas turbine engines, in which, for example, aerofoil components and casing structures may be made from composite materials.

Layered composite components comprise a resin matrix in which are embedded reinforcing layers, commonly in the form of plies of reinforcing fibres which may be unidirectional, woven, braided, non-crimp fabric or knitted.

Destructive methods of component testing are commonly employed for layered composite components. The component is cut into pieces so that its internal structure can be examined for manufacturing consistency and to check for flaws. Owing to the high statistical variability of composite materials, relatively large numbers of components are destroyed in order to provide a sufficient amount of data for reliable results, increasing costs and reducing the number of finished components available for sale or use. It is therefore desirable to employ non destructive methods in the testing of layered composite components.

It is known to use non destructive testing (NDT) methods such as C-scanning or acoustic emission for metal components. In an example test process, an acoustic signal is introduced into a test specimen, propagates through the specimen and is detected by a receiver. The path taken by the acoustic signal through the metal is well characterised, allowing any damage in the component to be accurately located Acoustic techniques are valuable tools in the testing of homogeneous metal components. However, the usefulness of such techniques is markedly reduced when employed for testing of layered composite components. The path taken by an acoustic signal through a layered composite component is confused by the multiple reflections and refractions that take place at each material interface. At every boundary, longitudinal and transverse components of a wave are both reflected and refracted, meaning a signal of unit amplitude is broken into four signals with some fraction of unity. The signal complexity resulting from multiple reflections and refractions can be compounded by individual fibre bundle arrangement, for example in the case of woven fibre bundles. By the time a signal has propagated through an entire composite component, the original signal is unrecognisable amidst the noise generated by the reflections and refractions, and determining when or from where the signal originated becomes impossible. In addition, random small variations in the laminate yield a phenomenon known mathematically as "localisation": the energy of an input signal becomes increasingly attenuated, or reflected back, as it penetrates into the component, such that the C-scan input signal can only penetrate the outermost layers. Manufacturing variations can therefore directly impact the effectiveness of acoustic techniques. Indeed, direct and suitably calibrated measurements of signal reflection and attenuation could provide a means to determine cured ply thickness variation, and thereby monitor manufacturing quality fluctuations.

It is known that composite materials can act as wave guides. On one length scale there are layers of material with different fibre directionality. On another length scale there are fibre tows and individual fibres. This aspect of material behaviour has a significant impact on the path taken by an acoustic signal through a composite, and can further complicate the process of determining where a signal has originated.

A further complication introduced when considering acoustic/ultrasound based NDT of layered composite components is that a great deal more information about the internal structure of the component is required in comparison to that needed for a metal component. The entire internal structure of a composite component needs to be verified, the composite lay up and fibre architecture need to be checked to ensure that fibre material is where it should be. In addition, any voids or resin rich areas need to be identified and variations in ply or layer thickness need to be checked.

According to the present invention, there is provided a method of identifying a region of a layered composite component that a test signal has passed through, comprising applying a label to the test signal as it passes through the region, such that the label applied to the test signal is indicative of the said region.

The test signal may be an acoustic signal. Alternatively, the test signal may be any other signal, for example light waves or electromagnetic waves, provided the selected signal is appropriate to the length scales of the material to be tested.

The step of applying a label to the acoustic signal may comprise filtering a predetermined frequency band out of the acoustic signal.

The method may further comprise the step of determining the dispersive nature of the region.

The dispersive nature of the region may be determined by correlating high and low frequency bands of the labelled acoustic signal and comparing the time of arrival of the high and low frequency bands at a sensor.

The layered composite component may comprise plies formed of bundles of reinforcing fibres embedded in a resin matrix.

The region may comprise at least one of a fibre bundle, a section of a ply and a ply.

The test signal may comprise a component part of a test signal introduced into the layered composite component.

According to another aspect of the present invention, there is provided a layered composite component wherein a region of the component is operable to label a test signal passing through that region.

The region may comprise an acoustic filter operable to filter a predetermined frequency band out of an acoustic test signal.

The component may comprise plies formed of bundles of reinforcing fibres embedded in a resin matrix.

The acoustic filter may comprise a groove extending across a bundle of fibres.

The acoustic filter may comprise a groove extending across a ply.

The acoustic filter may comprise apertures extending through a ply.

The acoustic filter may comprise pins extending through at least one ply.

For a better understanding of the present invention, and to show more clearly how it may be carried into effect, reference will now be made, by way of example, to the accompanying drawings, in which:—

Figure 1:
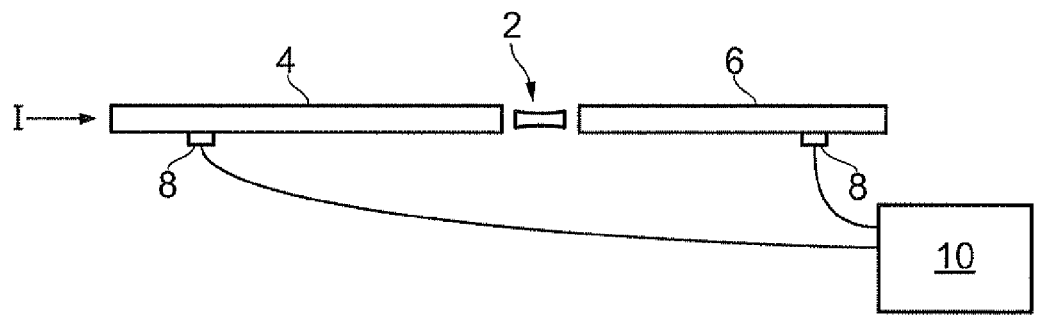
FIG. 1 is a schematic illustration of apparatus for the Hopkinson's Bar impact test.

As noted above, composite components act as wave guides on the ply scale and on the fibre scale, depending on the length scale of the acoustic signal. This aspect of the material behaviour has a significant impact on the path taken by an acoustic signal through a composite, and can further complicate the process of determining where a signal has originated. However, according to the present invention, the waveguide effect of composite components is actually employed to positive effect. When an incident wave hits an interface, the division of amplitude between reflected and refracted portions depends on the difference in properties between the materials on either side of the interface. For light waves propagating through optical media of different refractive indices, it is possible to get phenomena such as total internal reflection. For acoustic waves in solids the situation is more complicated, as there are longitudinal and transverse components of the wave front and these are shared differently at the interface. Nevertheless, for acoustic waves in a medium of relatively high Young's modulus, encountering an interface with a medium of relatively low Young's modulus, the majority of the amplitude of the wave is reflected back into the high Young's modulus layer. In composite components, the reinforcing fibres are of higher Young's modulus than the surrounding resin. Thus, waves travelling through composite components will tend to travel in the direction of the fibres making up the layers. The Young's modulus of a material also dictates the speed at which the wave will propagate (wave speed is proportional to the square root of Young's modulus), meaning that the first signals to arrive at a sensor will be those that have travelled through high Young's modulus material. In composites, where the Young's modulus of the fibres is 10 to 100 times that of the resin, the wave speed in the fibre direction is of order 3 to 10 times the speed against the fibre direction (when the wave has to propagate through resin). In practise, the only signals that will penetrate any distance from an acoustic source at a registrable level are fibre transmitted signals.

The fibres within a composite component thus represent a network of paths through which acoustic signals can travel. The present invention provides a means of identifying which signals have passed down which paths by applying a label to a signal as it passes along a specified section of a path. Once a signal has been given a label then it can be identified, even if it is of low strength and amongst a lot of noise.

The present invention thus employs the waveguide property of composite materials to beneficial effect. According to the present invention, by taking due account of this waveguide property of composite materials, a method for labelling signals passing through a composite component is provided that involves applying the mathematical understanding of processes involved in otherwise entirely unrelated materials testing techniques to consideration of wave propagation in composites.

The Hopkinson's Bar Impact Test, illustrated in FIG. 1, is a high strain rate material characterisation test. According to the Hopkinson's Bar Test, a sample 2 is mounted between two slender bars 4, 6. An impact/is transmitted to the input bar 4 and initiates a shock wave. The shockwave propagates along the input bar 4 and at the interface with the specimen, part of the wave is reflected back and part passes through the specimen and into the output bar 6, undergoing modifications as it passes through the specimen. The input pulse, reflected pulse and modified output pulse are recorded by strain gauges 8 and sent to a signal analyser 10. Analysis of the differences between the input, reflected and output pulses provides information as to the material properties of the specimen.

In the Hopkinson's Bar Impact Test, an assumption is made that the long, slender nature of the input bar ensures that the complex stress field generated at the impact end quickly transitions to a simple longitudinal pulse, so that a well characterised wave pulse is introduced into the specimen. In practice, for waves having a wavelength that is short in comparison to the radius of the bar, this assumption is not valid. Short wavelength waves can be significant in the transverse direction, causing through thickness vibration of the bar. This effect, sometimes known as the Poisson effect, is dispersive, meaning that wave speed is a function of wavelength. The dispersive effect causes transverse wave components to modify the shape of the wave front over time, complicating the wave pulse input to the test specimen.

Figure 2:
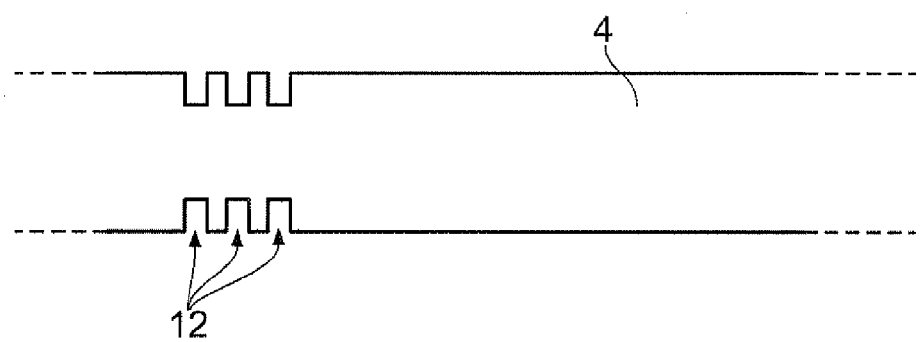
FIG. 2 is an exploded view of an input bar having a high frequency filter.
Figures 3A, 3B:
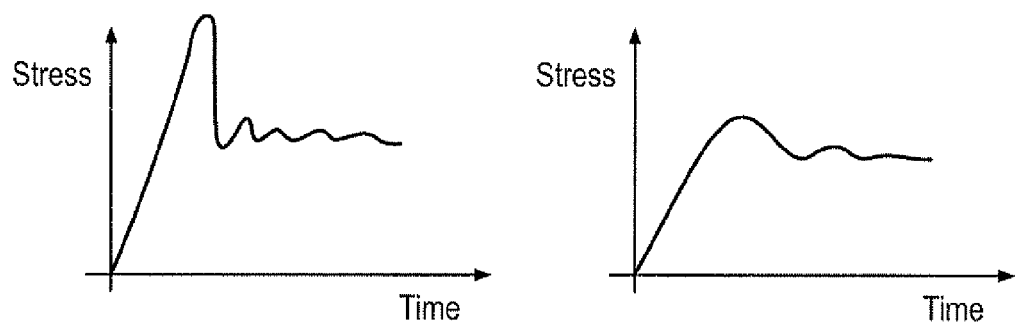
FIGS. 3a and 3b illustrate wave fronts with and without conditioning.

In order to filter out the undesirable short wavelength (high frequency) wave components, it is known to introduce a number of grooves into the input and/or output bars of a Hopkinson's Bar test apparatus, as illustrated in FIG. 2. The grooves 12 do not impede passage of a wave front comprising long wavelength elements. However, for shorter wavelength elements, of the order of, or shorter than the thickness of the bar, the grooves act as a filter, interacting with and dissipating the short wavelength wave elements. The process of filtering out the high frequency wave components is known as conditioning. An impact signal without conditioning is illustrated in FIG. 3a, in which high frequency elements can be seen. FIG. 3b shows the same signal with conditioning, the high frequency elements having been filtered out.

By considering fibre bundles as analogous to rods or bars, the present invention takes the mathematical foundation and understanding of the Hopkinson's Bar Test and advantageously applies it to the consideration of acoustic wave propagation through fibre bundles in a composite material.

Figure 4:
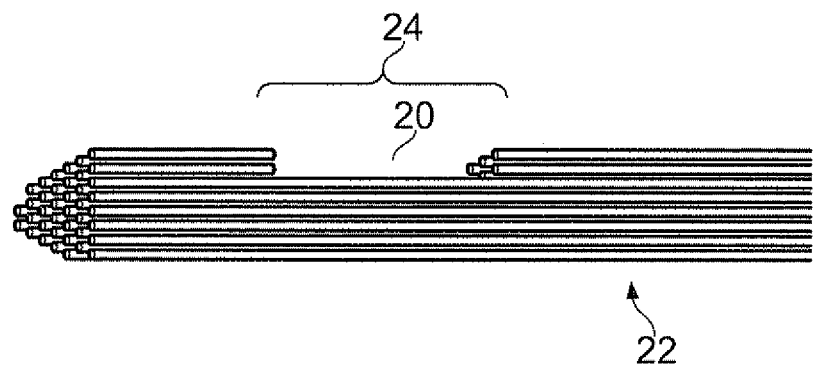
FIG. 4 illustrates a fibre bundle.

Thus, according to one embodiment of the present invention, a label is applied to a signal passing through a composite component by filtering out a specific frequency band of the signal as it is transmitted through the fibre bundles. Once labelled in this manner, the signal can be identified by a receiver, even if it is of low amplitude and among a lot of noise. FIG. 4 illustrates how a filter can be incorporated into a fibre bundle of a component. A series of grooves 20 are formed in a fibre bundle 22. The grooves 20 act to filter out high frequency signal components passing along the fibre bundle. The grooves interact with and dissipate the high frequency elements as they propagate through the fibre bundle. The filter 24 can be placed at a specific location within a fibre bundle, or at multiple locations within the same bundle. Different filters may be employed in different bundles in order to differentiate between different paths that may be taken through the composite component.

Figure 5A:
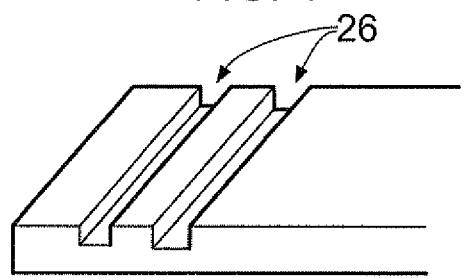
FIGS. 5a to 5c illustrate plies of a layered composite component.
Figure 5B:
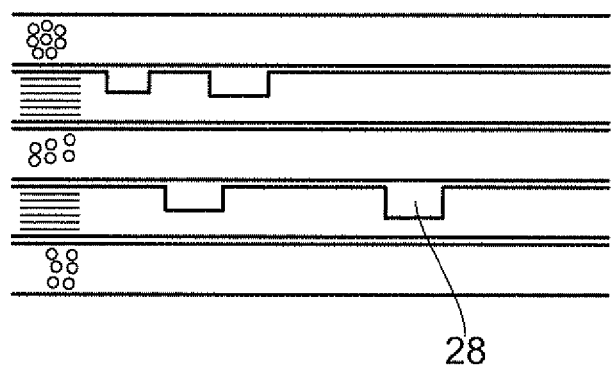
Figure 5C:
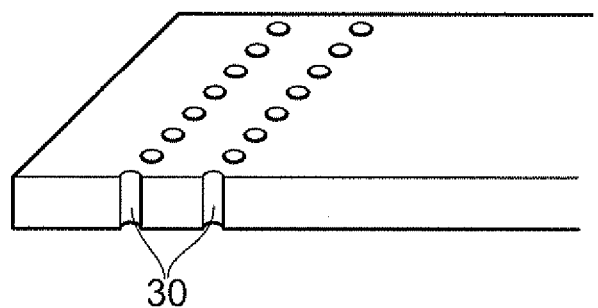

FIG. 5 illustrates how a filter can be incorporated into a ply length. Notches or grooves 26 as illustrated in FIG. 5a extend across the width of the ply and act to filter out high frequency components of an acoustic signal. These grooves 26 result in resin rich areas 28 when the plies are stacked together, and extend across the fibre direction, as indicated by the parallel lines and circles on the left of FIG. 5b. In an alternative arrangement, holes 30 are punched through a ply as illustrated in FIG. 5c. These holes have a similar filtering effect to the grooves 26 but maintain a greater proportion of the ply intact, thus reducing the impact of the filter on overall ply strength. Different configurations of grooves or holes filter our different frequency bands, thus providing unique identifying labels to signals propagating past the filter.

In another alternative arrangement (not shown), a technique such as Z pinning is employed to introduce pins of different material (for example metal) or of differently oriented material (for example carbon) into a ply. The pins influence the signal, having a signal modifying or filtering effect. The pins may be inserted in different sizes or numbers in different regions of the component. Each different configuration of pins has a different signal modifying effect, thus enabling a signal analyser to determine precisely which regions a signal has passed through.

Figure 6:
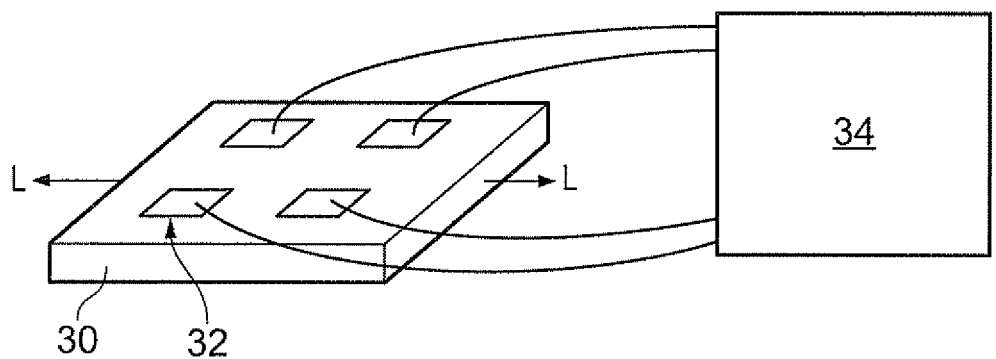

Once a signal has been labelled, enabling it to be identified even when of low amplitude and among a lot of noise, a range of information can be obtained from the signal. FIG. 6 illustrates a test arrangement. A component or test piece 30 is subjected to some form of loading L, which may either be a general engineering load, or a specific force, such as an impact, designed to set an acoustic pulse running through the component 30. Attached to the component 30 is at least one sensor 32, capable of detecting signals resulting from the load application. Alternatively, non-contacting optical or thermal methods can be employed to detect strain fields on the component. Signals from the sensor 32 are directed to a signal analyser 34.

Correlation techniques, including cross- and auto-correlation, are conventionally used to analyse changes in the nature of received signals over time and to determine the length of time taken for a signal to traverse a particular path, the "path length". As a signal is broken into multiple components at various material boundaries, different components of a signal will take different physical routes through the component, and will arrive at the sensor at different times. The signal analysis equipment "recognises" component parts of the same signal and outputs the differences in arrival time of the various component parts. Ordinarily, when using correlation techniques with composite components, the number of material boundaries, and hence the number of reflected and refracted signal components, leads to vast numbers of correlations, such that it is impossible to match output path length differences with actual physical routes, or to identify individual signal components. In addition, the dispersive nature of composites means that each signal component is modified with time. According to the present invention, signal components are labelled as they pass through specific fibre bundles and/or regions of a ply, thus enabling the physical path taken by a signal to be determined simply by analysing the labels applied to a signal. In this manner, different frequency components of the same signal, separated over time due to the dispersive effect of the material, can be identified and matched up as they are detected at the sensor. By labelling the signal components, the present invention allows for a practical application of the dispersive effect, providing further information about the component.

The amount of dispersion in a signal indicates a combination of how long it has been travelling and the dispersive nature of the route that it has traversed through. If the input signal was deliberately given, then the start point and path lengths for every arrival can be deduced, but if the signal was caused by acoustic emission (a crack initiation for example), then it is desirable to be able to pin-point its location. The labels applied to signal elements as they pass through a component according to the present invention enable analysis to separate out the effects of path length and material nature in causing dispersion. Signal labels indicate the regions that a signal has passed through and hence the physical path that it has followed. By correlating the lower frequency band of a signal, differences in arrival time, and therefore in path length, can be identified. The labels applied to the signal are used to associate path lengths with the specific physical paths taken by the signals. The higher frequency band of a signal can also be correlated and its arrival time compared to that of the corresponding low frequency band. Information as to the dispersive nature of the path taken by the signal can then be determined (dispersion causing the propagation speed of the wave to vary with wavelength).

In most cases, the amount of dispersion will relate to the relative "lateness" of arrival of the high frequency band of the signal. However, "lateness" may also be an indication of significant differences in the nature of the material encountered by the different parts of the signal. For example, one part of the signal may have come through a narrow layer in the composite, while the other part may have come through a double layer (two plies stacked in the same orientation). In the frequency range relating to a wavelength of the order of the ply thickness, the dispersion characteristic would be different. Knowing the ply stack arrangement of the component, it would then be possible to deduce where the signal initiated from.

In a composite component, it is usually desirable to achieve a very even cured ply thickness (i.e. each ply of similar material should end up being the same thickness after curing). Differences in signal dispersion characterise the variability in cured ply thickness. This information is currently only available by cut-up or CT scanning (x-ray tomography), and quality of data is limited by the component size as large components are scanned at lower resolution. There is a cost limitation, and a practical size limit. The present invention thus provides a practical alternative manner of obtaining this information.

In the case of the use of techniques such as acoustic emission, where the acoustic wave initiation site is unknown, it is desirable to get an indication of the baseline dispersion for a certain path distance. In this case, a further test is undertaken, which involves applying a shock wave pulse (impact or sound wave source) at a given location, and studying the level and type of dispersion seen in signals received at a known distance (and time interval) away.

It will be appreciated that the present invention can be employed as a research or analysis tool as well as for component NDT. As a research or analysis tool, the present invention may be used to explore the inner structure of a composite component, for example to enhance understanding of the manufacturing process and to assist in validation of computational methods.

In the field of production NDT, the present invention in effect provides a physical "finger print" within the component, enabling the determination of one of more of the following:

(i) the positional accuracy of key plies
(ii) the variation in thickness of specific plies
(iii) the variation in fibre alignment
(iv) the presence of voids or other inclusions.

The present invention can be employed for example with known C-scanning methods, enhancing the effectiveness of these methods for composite components and thus reducing reliance on more expensive methods such as x-ray CT scanning.

The invention claimed is:

1. A method of testing a layered composite component, the method comprising:
   providing an acoustic filter in at least two layers of the composite component, each acoustic filter operable to filter a different predetermined frequency band out of an acoustic test signal;
   applying an acoustic test signal to the composite component;
   detecting the acoustic test signal after it has passed through the composite component; and analyzing differences between the applied signal and the detected signal to determine which layers the applied signal has passed through.

2. A method as claimed in claim 1, further comprising the step of determining the dispersive nature of the composite component in a region through which the acoustic test signal has passed.

3. A method as claimed in claim 2, wherein the dispersive nature of the region is determined by correlating high and low frequency bands of the acoustic test signal and comparing the time of arrival of the high and low frequency bands at a sensor.

4. A method as claimed in claim 1, wherein the layered composite component comprises plies formed of bundles of reinforcing fibers embedded in a resin matrix.

5. A method as claimed in claim 1, wherein a sensor for detecting the acoustic test signal after it has passed through the composite component is positioned on an external surface or external to the composite component.

6. A layered composite component in which an acoustic filter is provided in at least two layers, each acoustic filter operable to filter a different predetermined frequency band out of a single acoustic test signal, wherein the component comprises plies formed of bundles of reinforcing fibers embedded in a resin matrix.

7. A layered composite component as claimed in claim 6, wherein at least one of the acoustic filters comprises a groove extending across a bundle of fibers.

8. A layered composite component as claimed in claim 6, wherein at least one of the acoustic filters comprises a groove extending across a ply.

9. A layered composite component as claimed in claim 6, wherein at least one of the acoustic filters comprises apertures extending through a ply.

10. A layered composite component as claimed in claim 6, wherein at least one of the acoustic filters comprises pins extending through at least one ply.

* * * * *